(12) United States Patent
Brock-Fisher

(10) Patent No.: US 6,497,661 B1
(45) Date of Patent: Dec. 24, 2002

(54) PORTABLE ULTRASOUND DIAGNOSTIC DEVICE WITH AUTOMATIC DATA TRANSMISSION

(75) Inventor: George A. Brock-Fisher, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/917,925

(22) Filed: Jul. 31, 2001

(51) Int. Cl.[7] .................................................. A61B 8/00
(52) U.S. Cl. ........................ 600/437; 600/447; 128/920; 128/923; 73/620
(58) Field of Search .............................. 600/437, 447; 128/923, 920; 73/620

(56) References Cited

U.S. PATENT DOCUMENTS

| | | | | |
|---|---|---|---|---|
| 4,246,792 A | * | 1/1981 | Matzuk | 73/620 |
| 5,740,801 A | * | 4/1998 | Branson | 128/920 |
| 5,957,846 A | * | 9/1999 | Chiang et al. | 600/447 |
| 6,283,761 B1 | * | 9/2001 | Joao | 128/923 |
| 2002/0028995 A1 | * | 3/2002 | Mault | 600/437 |

* cited by examiner

*Primary Examiner*—Marvin M. Lateef
*Assistant Examiner*—Ruby Jain
(74) *Attorney, Agent, or Firm*—John Vodopia

(57) ABSTRACT

A portable ultrasound diagnostic device dynamically collecting diagnostic data from a patient and, once the portable ultrasound diagnostic device determines that collecting the diagnostic data is complete, the portable ultrasound diagnostic device transmits the diagnostic data using a communication channel to a person at another location to analyze the diagnostic data.

36 Claims, 2 Drawing Sheets

PORTABLE ULTRASOUND DIAGNOSTIC DEVICE WITH AUTOMATIC DATA TRANSMISSION

BACKGROUND OF THE INVENTION

With the advent of miniaturized digital technology, it is now possible to reduce the size of diagnostic devices to a hand-held or portable case-like size. For instance, it is now possible to reduce the size of an oscilloscope to a device that fits in the palm of one's hand. Also, diagnostic ultrasound imaging devices are also being produced which are small enough to carry as readily as a book. The diagnostic data obtained by these devices is typically an image or graphical display or numerical data.

The convenience which these smaller, lighter devices offer results in their expanded use, often times by persons less skilled than in the past. Specifically, rescuers in an emergency situation may be required to use portable ultrasound diagnostic devices, such as a hand-held oscilloscope, to perform specific diagnostic procedures. However, once the rescuers obtain the diagnostic data from a patient using the diagnostic device, often times these rescuers do not have adequate training to determine from the diagnostic data a medical treatment the patient needs. Thus, while persons less skilled can obtain the diagnostic data, assessment of the diagnostic data obtained needs to be performed by someone not present at the field examination.

Accordingly, the rescuer or user would read the diagnostic data from an ultrasound device or oscilloscope and enter the data in a personal computer (PC), for instance, which requires a certain degree of expertise from the user. Further, manually entering the diagnostics obtained from either an ultrasound device or oscilloscope into the PC creates an uncertain degree of inaccuracy and mistake. While portable ultrasound diagnostic devices exist with serial interfaces, these devices require a connection to a PC to a serial interface, and therefore, require a person skilled in the use of specialized software to run the PC to extract the diagnostic data from the hand-held diagnostic device.

Thus, it is necessary to develop an evaluation system allowing for individualized evaluation configurations and a centralized hierarchy so large computer resources are not necessary at the user's end in order to make an adequate determination of the treatment for the patient, for instance, based on diagnostic data obtained from the patient. The evaluation system may also be used to obtain evaluation configurations from devices or systems such as electronic devices or vehicles. Further, an evaluation system is needed that allows authorized users to enter new diagnostic data and edit and view existing diagnostic data, including searching for diagnostic data within available databases at another location.

SUMMARY OF THE INVENTION

In an exemplary embodiment, the present invention provides for an apparatus including a portable ultrasound diagnostic device dynamically collecting diagnostic data and transmitting the diagnostic data using a communication channel to a person at another location to analyze the diagnostic data.

The present invention also provides an apparatus including a portable ultrasound diagnostic device dynamically collecting diagnostic data from a patient; and a user interface where a user commands the portable ultrasound diagnostic device to transmit the diagnostic data via a communication channel in the portable ultrasound diagnostic device once collecting the diagnostic data from the patient is complete, to a person at another location to analyze the diagnostic data.

The present invention is also achieved by a method including connecting a portable ultrasound diagnostic device to a patient; dynamically collecting diagnostic data from the patient; transmitting the diagnostic data using a communication channel to a person at another location once collecting the diagnostic data from the patient is complete; and receiving and analyzing the diagnostic data.

The present invention is also achieved by a method including connecting a portable ultrasound diagnostic device to a patient; dynamically collecting diagnostic data from the patient; connecting the portable ultrasound diagnostic device to a connector once collecting the diagnostic data from the patient is complete; transmitting the diagnostic data using a communication channel to a person at another location; and analyzing the diagnostic data and determining therefrom a medical treatment for the patient.

BRIEF DESCRIPTION OF THE DRAWINGS

Advantages of the invention will become apparent and more readily appreciated for the following description of the preferred embodiments, taken in conjunction with the accompanying drawings of which.

DETAILED DESCRIPTION OF THE INVENTION

Figure 1:
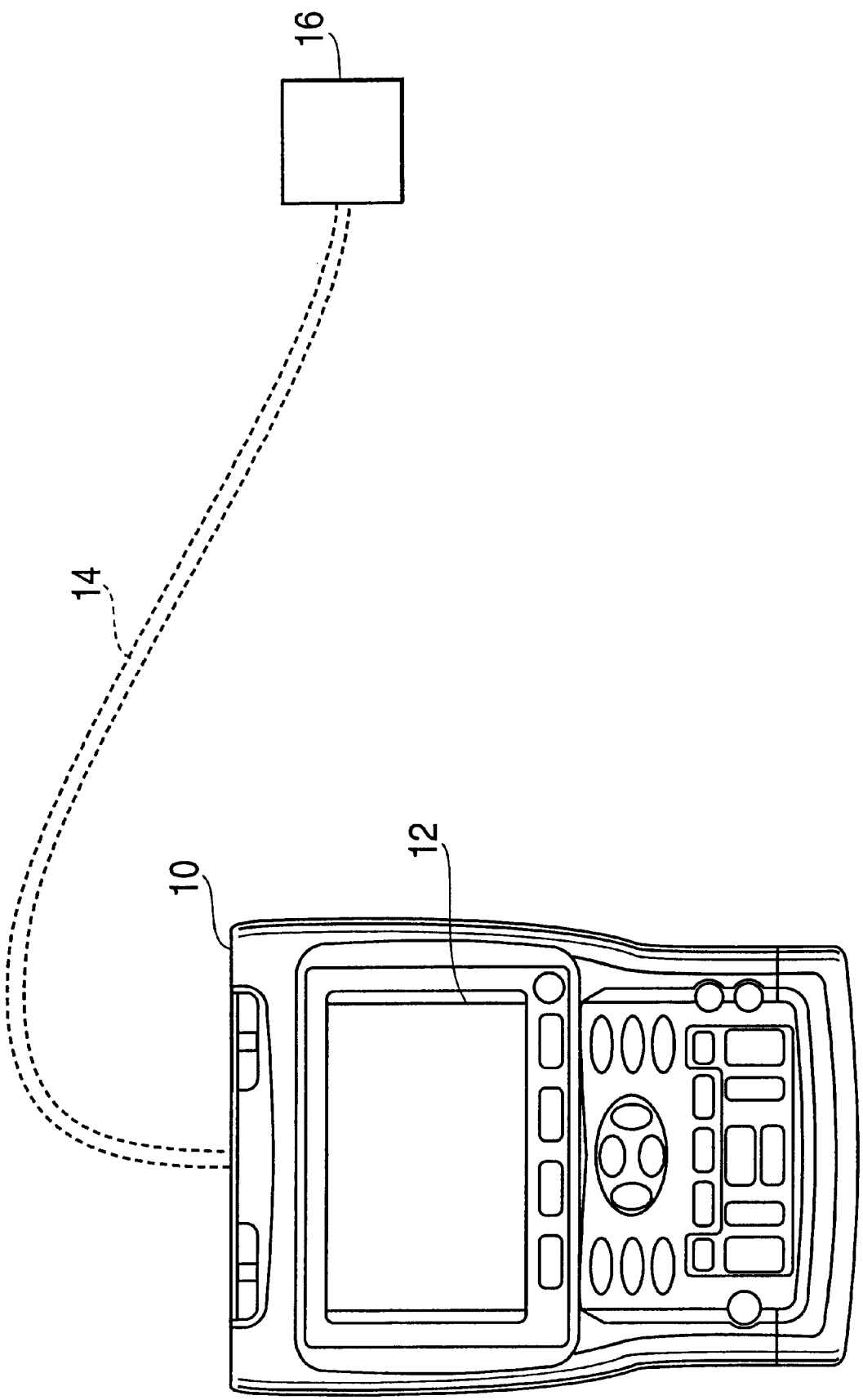
FIG. 1 illustrates a general system overview for an embodiment of the present invention.

Reference will be now made in detail to the present exemplary embodiments of the present invention, examples of which are illustrated in the accompanying drawings, wherein like reference numerals refer to the like elements throughout.

The present invention provides for the addition of one or more common types of data interface to a portable ultrasound diagnostic device, such as a hand-held oscilloscope to transmit acquired diagnostic image data, graphical data, or numerical data of a patient to another location. In accordance with an exemplary embodiment of the present invention, the portable ultrasound diagnostic device includes a telephone or Internet connection or wireless modem for transmitting the diagnostic data directly to another location.

FIG. 1 is a schematic diagram of an embodiment of a system including a portable ultrasound diagnostic device 10, in accordance with the present invention. The portable ultrasound diagnostic device 10 includes hand carry, hand use, or hand-held devices. In an exemplary embodiment, the present invention is described using the portable ultrasound diagnostic device 10, such as a hand-held oscilloscope. However, those skilled in the art will recognize that any other implementations of portable diagnostic devices or other types of hand-held devices may be used, such as ultrasound devices, blood pressure meters, reaction time meters, electroencephalographical oscilloscopes, cardiac resuscitation apparatuses, pulse rate meters, general purpose electronic scopes, etc.

The portable ultrasound diagnostic device 10 is embodied, for example, as a hand-held personal computer (H/PC) having an LCD touch screen, a keypad, and a communication channel (not shown). In the alternative, the portable ultrasound diagnostic device 10 may include, for example, a pointing member, such as a stylus or user's finger or thumb, and may be connected to an external keyboard. In other implementations, the handheld input device 10 may be implemented as a personal digital assistant (PDA), a palm-top computer, or other computing device. In an exemplary embodiment, the portable ultrasound diagnostic device 10 includes a screen 12 where the user would be able to determine whether a process of collecting the diagnostic data is complete or whether the diagnostic data obtained is enough to make an adequate diagnosis of the treatment the patient would require.

Once the user connects the portable ultrasound diagnostic device 10 to the patient and the portable ultrasound diagnostic device 10 is turned ON, the portable ultrasound diagnostic device 10 would run a program collecting diagnostic data from the patient. The portable ultrasound diagnostic device 10 dynamically, that is, in an automated manner using a computer processor, obtains diagnostic data from the patient and stores the diagnostic data in a permanent or removable storage unit, such as magnetic and optical discs, RAM, ROM, etc. on which the data can be stored and distributed. The diagnostic data includes, for example, an image, a graphical image of an organ of the patient, or a numerical measurement (voltage or heart rate).

Once the portable ultrasound diagnostic device 10 is done collecting the diagnostic data, the user then connects, using a communication cable 14, the portable ultrasound diagnostic device 10 from the portable ultrasound diagnostic device 10 to a telephone connector or docketing station 16, thereby connecting to a business intranet connection, facsimile, or Internet at another location. Although FIG. 1 shows the communication cable 14 connecting to the telephone connector or the like, those skilled in the art will appreciate that alternative communication channels may be used, such as an infrared (IR) port, a telephone modem, a wireless modem, or business intranet connection. The user commands the portable ultrasound diagnostic device 10 using a user interface, such as a screen or a button or the like on the portable ultrasound diagnostic device 10 to transmit the diagnostic data via the communication channel connected to the telephone connector or docketing station 16 to a person, such as a doctor or expert at another location.

In the alternative, once the portable ultrasound diagnostic device 10 determines that collecting the diagnostic data is complete, the portable ultrasound diagnostic device 10 may automatically transmit the diagnostic data to another location using a wireless modem, thereby eliminating the time required to connect the portable ultrasound diagnostic device 10 to a phone line connection. In the alternative, upon command from the user, the portable ultrasound diagnostic device 10 may transmit the diagnostic data to another location using the wireless modem.

The diagnostic device might also, for example, allow authorized users to enter new patient data and edit and view existing patient data, including searching for patient data within available databases at another location. Further, the portable ultrasound diagnostic device 10 may be programmed to dynamically dial a particular telephone number and transmit the data to a PC under the expert's control or transmit the diagnostic data using facsimile encoding or transmit the diagnostic data to the expert using a pre-stored Internet web address. In the alternative, the user may directly dial the telephone number or enter the Internet web address of the expert using the user interface in the portable ultrasound diagnostic device or a keyboard, a mouse, or the like.

At another location, the expert, such as a cardiologist, retrieves the diagnostic data via the PC, a fax machine, or the like and determines therefrom a treatment for the patient. The diagnostic data may be in graphical, wave, or numerical form. Thus, in the event that there is a limited number of individuals that know how to determine from the diagnostic data the type of treatment the patient needs, the portable ultrasound diagnostic device 10 provides flexibility where the expert may be at a remote location and multiple users may communicate with the expert thereby providing a system that is effective in providing adequate assistance to individuals in an emergency or other type of situation.

Upon review of the diagnostic data, the expert may communicate with the user and make recommendations as to the treatment the patient would require. In the event that the diagnostic data is not sufficient for the expert to make an adequate determination of the treatment the patient needs, the present invention allows continuous communication between the expert and the user via the telephone and the portable ultrasound diagnostic device 10, thereby significantly reducing the risk of misdiagnosing or not providing the patient with the adequate medical treatment. The user may obtain additional data and transmit new diagnostic data to the expert; thereby the diagnostics may be repeated until the patient is stabilized.

Figure 2:
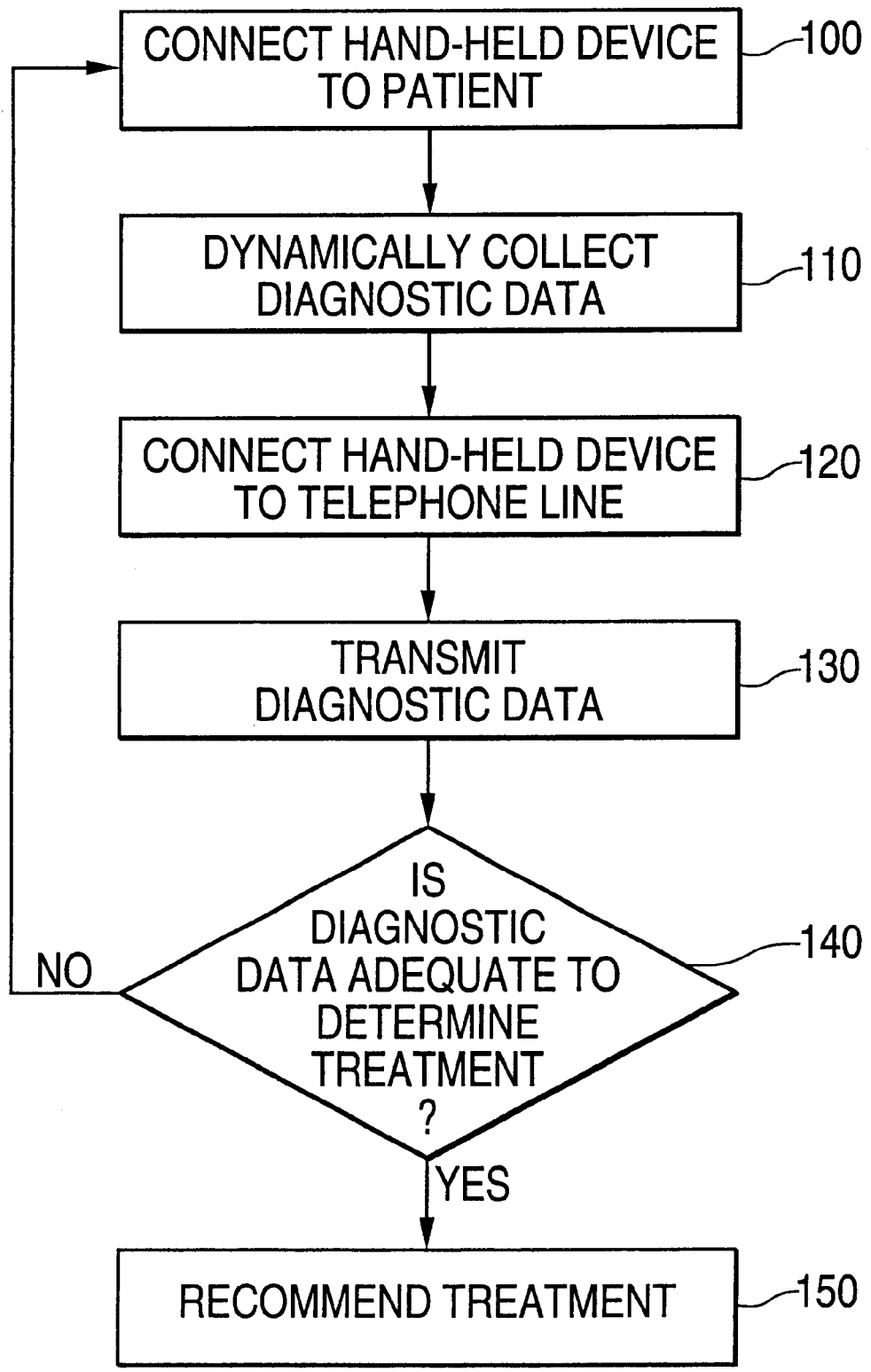
FIG. 2 is a flow chart illustrating a method embodiment of the present invention.

As illustrated in FIG. 2, a flow chart illustrating a method embodiment of the present invention is shown. At operation 100, a user connects the portable ultrasound diagnostic device 10 to the patient. At operation 110, the portable ultrasound diagnostic device 10 dynamically collects diagnostic data. At operation 120, once collecting the diagnostic data is complete, the user would connect the portable ultrasound diagnostic device 10 to a telephone line. At operation 130, the portable ultrasound diagnostic device 10 automatically transmits the diagnostic data to the expert at another location using the communication channel on the portable ultrasound diagnostic device 10 to analyze the diagnostic data. In the alternative, the user may command the portable ultrasound diagnostic device 10 to transmit the diagnostic data to the expert at another location. At operation 140, if the diagnostic data is adequate to determine a medical treatment for the patient, then, at operation 150, the expert recommends the medical treatment for the patient to the user. Otherwise, from operation 140, the method returns to operation 100 where the expert requests the user, via the telephone for instance, to either check the connections of the portable ultrasound diagnostic device to the patient or repeat the procedure to dynamically obtain the diagnostic data.

Thus, the present invention provides for a portable ultrasound diagnostic device that, once the user connects the device to patient, the device dynamically obtains diagnostic data from the patient. Further, the portable ultrasound diagnostic device allows transmission of the diagnostic data to an expert at another location, thereby substantially eliminating human error.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An apparatus comprising:
   a portable ultrasound diagnostic device automatically collecting diagnostic data from a patient and, once the portable ultrasound diagnostic device determines that collecting the diagnostic data is complete, the portable ultrasound diagnostic device transmits the diagnostic data using a communication channel to at another location for analysis of the diagnostic data, the portable ultrasound diagnostic device configured for enabling continuous communication via the communication channel for receiving at least one command requesting additional diagnostic data to be transmitted until all the transmitted diagnostic data is determined to be adequate for providing a diagnosis.

2. The apparatus as recited in claim 1, wherein the portable ultrasound diagnostic device automatically accesses a pre-stored Internet web address and transmits the diagnostic data to the person.

3. The apparatus as recited in claim 1, wherein the portable ultrasound diagnostic device transmits the diagnostic data automatically using the communication channel.

4. The apparatus as recited in claim 1, wherein the communication channel comprises one of a communication cable, an infrared (IR) port, a telephone modem, a wireless modem, and business intranet connection.

5. The apparatus as recited in claim 1, wherein the portable ultrasound diagnostic device automatically determines when collecting the diagnostic data from the patient is complete.

6. The apparatus as recited in claim 1, wherein the diagnostic data comprises one of an image, graphical readout, and a numerical measurement.

7. The apparatus as recited in claim 1, wherein the portable ultrasound diagnostic device comprises a storage unit storing the diagnostic data.

8. The apparatus as recited in claim 1, wherein the portable ultrasound diagnostic device dials a pre-stored telephone or facsimile number and through the communication channel, transmits the diagnostic data to a PC or a fax machine for analysis of the diagnostic data.

9. The apparatus as recited in claim 1, wherein the portable ultrasound diagnostic device comprises an LCD touch screen, a keypad, and a communication channel.

10. The apparatus as recited in claim 1, wherein the portable ultrasound diagnostic device is connected to an external keyboard and comprises an LCD touch screen and a pointing member.

11. The apparatus as recited in claim 1, wherein the portable ultrasound diagnostic device is a hand-held oscilloscope.

12. An apparatus comprising:
a portable ultrasound diagnostic device automatically collecting diagnostic data from a patient;
a user interface where a user commands the portable ultrasound diagnostic device to transmit the diagnostic data via a communication channel once collecting the diagnostic data from the patient is complete, to another location for analysis of the diagnostic data; and
means for enabling continuous communication via the communication channel for receiving at least one command requesting additional diagnostic data to be transmitted until all the transmitted diagnostic data is determined to be adequate for providing a diagnosis.

13. The apparatus as recited in claim 12, wherein the communication channel comprises one of a communication cable, an infrared (IR) port, a telephone modem, a wireless modem, and business intranet connection.

14. The apparatus as recited in claim 12, wherein the user directs the portable ultrasound diagnostic device to transmit the diagnostic data by dialing a telephone number, a facsimile number, or entering an Internet web address using a user interface in the portable ultrasound diagnostic device, a keyboard, or a mouse.

15. The apparatus as recited in claim 12, wherein the portable ultrasound diagnostic device comprises a storage unit storing the diagnostic data.

16. The apparatus as recited in claim 13, wherein the diagnostic data comprises one of an image, graphical readout, and a numerical measurement.

17. The apparatus as recited in claim 12, wherein the portable ultrasound diagnostic device automatically dials a pre-stored telephone or facsimile number and through the communication channel, automatically transmits the diagnostic data to a PC or a fax machine for analysis of the diagnostic data.

18. The apparatus as recited in claim 12, wherein the portable ultrasound diagnostic device automatically accesses a pre-stored Internet web address and transmits the diagnostic data.

19. The apparatus as recited in claim 12, wherein the portable ultrasound diagnostic device comprises a hand-held oscilloscope.

20. A method comprising:
connecting a portable ultrasound diagnostic device to a patient;
automatically collecting diagnostic data from the patient;
transmitting the diagnostic data using a communication channel during a communication session to another location once collecting the diagnostic data from the patient is complete;
receiving the transmitted diagnostic data and determining if the transmitted diagnostic data is adequate for providing a diagnosis;
repeating the collecting and transmitting steps during the communication session if the transmitted diagnostic data is determined not be adequate; and
analyzing the transmitted diagnostic data.

21. The method as recited in claim 20, wherein the diagnostic data is automatically transmitted from the portable ultrasound diagnostic device once collecting the diagnostic data from the patient is complete.

22. The method as recited in claim 20, further comprising viewing and editing existing diagnostic data within available databases at another location.

23. The method as recited in claim 20, further comprising storing the diagnostic data.

24. The method as recited in claim 20, wherein the transmitting the diagnostic data dials a pre-stored telephone or facsimile number through the communication channel and transmits the diagnostic data in accordance with the pre-stored telephone or facsimile number.

25. The method as recited in claim 20, wherein the portable ultrasound diagnostic device comprises a hand-held oscilloscope.

26. The method as recited in claim 20, wherein the transmitting the diagnostic data automatically accesses a pre-stored Internet web address and transmits the diagnostic data.

27. The method as recited in claim 20, wherein the communication channel comprises one of a communication cable, an infrared (IR) port, a telephone modem, a wireless modem, and business intranet connection.

28. A method comprising:
connecting a portable ultrasound diagnostic device to a patient;
automatically collecting diagnostic data from the patient;
connecting the portable ultrasound diagnostic device to a connector once collecting the diagnostic data from the patient is complete;

transmitting the diagnostic data using a communication channel during a communication session to another location;

analyzing the diagnostic data and determining therefrom if a diagnosis of the patient can be made for determining a medical treatment for the patient; and receiving additional diagnostic data from the portable ultrasound diagnostic device during the communication session if it is determined that a diagnosis of the patient cannot be made; and determining from the received diagnostic data a medical treatment for the patient.

29. The method as recited in claim 28, wherein the diagnostic data is automatically transmitted from the portable ultrasound diagnostic device once collecting the diagnostic data from the patient is complete.

30. The method as recited in claim 28, further comprising viewing and editing existing diagnostic data within available databases at another location.

31. The method as recited in claim 28, wherein the transmitting the diagnostic data dials a pre-stored telephone or facsimile number through the communication channel and transmits the diagnostic data in accordance with the pre-stored telephone or facsimile number.

32. The method as recited in claim 28, wherein the transmitting the diagnostic data automatically accesses a pre-stored Internet web address and transmits the diagnostic data.

33. The method as recited in claim 29, wherein the communication channel comprises one of a communication cable, an infrared (IR) port, a telephone modem, a wireless modem, and business intranet connection.

34. The method as recited in claim 28, wherein the connector comprises a telephone connector or a docketing station connected to one of a business intranet, facsimile, and Internet at another location.

35. The method as recited in claim 28, wherein the portable ultrasound diagnostic device comprises a hand-held oscilloscope.

36. The method as recited in claim 28, further comprising storing the diagnostic data.

* * * * *